(12) United States Patent
Thayer, Jr.

(10) Patent No.: US 6,429,334 B1
(45) Date of Patent: Aug. 6, 2002

(54) PRODUCTION OF ACID ANHYDRIDES AND ACID CHLORIDES

(75) Inventor: Gordon L. Thayer, Jr., Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/588,883

(22) Filed: Jun. 7, 2000

(51) Int. Cl.[7] .......................... C07C 51/60; C07C 51/58
(52) U.S. Cl. .................. 562/846; 562/857; 562/859
(58) Field of Search ................................ 562/846, 859

(56) References Cited

U.S. PATENT DOCUMENTS

| 3,337,622 A |   | 8/1967 | Brotherton |
|---|---|---|---|
| 4,623,491 A | * | 11/1986 | Siegemund et al. |
| 5,113,016 A |   | 5/1992 | Seagraves .................. 562/856 |
| 6,002,043 A |   | 12/1999 | Descorps et al. |

FOREIGN PATENT DOCUMENTS

| GB | 371946 | 5/1932 |   |
|---|---|---|---|
| JP | 51040041 B | 11/1976 |   |
| JP | Sho 56-103134 | 8/1981 | ........... C07C/53/38 |
| JP | 56103314 A | 8/1981 |   |
| JP | 57007438 B | 1/1982 |   |

* cited by examiner

Primary Examiner—Paul J. Killos
Assistant Examiner—Robert W. Deemie

(57) ABSTRACT

A process that can be used to produce an acid anhydride or acid chloride is provided. The process comprises contacting a reaction medium with a catalyst. The reaction medium comprises at least one organic acid, combination of the organic acid and phosgene, combination of at least one organic anhydride and phosgene, or combinations of the organic acid, the organic anhydride, and phosgene. The reaction medium can further comprise a solvent. The catalyst is a Group IVB transition metal halide.

28 Claims, No Drawings

PRODUCTION OF ACID ANHYDRIDES AND ACID CHLORIDES

FIELD OF THE INVENTION

The invention relates to a process that can be used for producing an organic anhydride, an organic acid halide, or combinations thereof.

BACKGROUND OF THE INVENTION

Acid anhydrides and acid chlorides are important intermediates for the chemical industry.

Aliphatic and aromatic acid anhydrides have a variety of chemical uses, including the preparation of certain esters, such as cellulose esters and aspirin; the manufacture of alkyd resins; modification of the curing of certain epoxy resins and of polyester properties; as a retarder in rubber vulcanization; and in various syntheses, such as those of phenolphthalein, polypeptides, and peroxycarboxylic acids.

Acid chlorides, such as isophthaloyl and terephthaloyl chlorides are important polymer intermediates, for instance in the production of polymers for fibers and polycarbonates. Such applications require very low levels of impurities and by-products. Monofunctional contaminants can seriously reduce the molecular weight of a polyester and adversely affect the physical properties of fibers spun from the polymer. Traces of colored impurities can be unacceptable in polycarbonate products intended for optical uses.

Isophthaloyl chloride can be prepared from isophthalic acid by many routes. Commercially, the preferred chlorinating agent is phosgene, as described by Carnahan in U.S. Pat. No. 2,657,233. The uncatalyzed or "thermal" reaction is, however, slow. A problem is that, as the temperature is raised, the solubility of phosgene in the liquid phase decreases, limiting the acceleration of the reaction.

Consequently, numerous catalytic systems have been proposed for the reaction of acids with phosgene to produce the acid chlorides. A number of nitrogen containing compounds, e.g., amides and ureas are in use. An important example is dimethylformamide (hereinafter DMF) as described by Seagraves in U.S. Pat. No. 5,113,016. The active catalyst in the DMF process is the reaction product of DMF and phosgene. This material is thermally unstable, decomposing rapidly above 100° C., especially in the absence of excess acid.

Thus, the MF/phosgene complex is only marginally stable under the reaction conditions, and impurities such as formylbenzoyl chloride and dichlorotoluoyl chloride are formed. Seagraves, in U.S. Pat. No. 5,113,016, cited above, reduced the amount of these impurities by introducing an oxidizing air sparge into the process. Other nitrogen-containing catalysts also have the disadvantage of marginal stability under the reaction conditions. Essentially all the impurities in the product using the DMF catalyst result from decomposition of the DMF catalyst. Japanese Patent Kokai: Sho 56-103134, Nagata, et al discloses a purification procedure involving the addition of certain metals and their salts, including titanium and titanium chloride, to the reaction product formed by the reaction of organic carboxylic acids and phosgene using lower aliphatic amides as the catalyst.

Decomposition of the DMF catalyst results in emissions of methyl chloride. Methyl chloride is of environmental concern as a "greenhouse gas". It also results in the formation of dimethylcarbamoyl chloride, a carcinogen, requiring responsible disposal, and careful control in the product. DMF decomposition further results in a tar purge stream requiring appropriate disposal and causing a yield loss.

Finally, the DMF catalyst species is very corrosive, increasing the cost of materials of construction.

Other processes have been proposed using phosphorus compounds, nitrogen heterocyclic compounds, amines, and other catalysts. All possess some combination of disadvantages, high cost, higher reaction temperatures, lower yields, etc.

It would be desirable to develop a process for using organic acids to form the anhydride and, in the presence of phosgene, to form the acid chloride. The present invention provides such a process.

SUMMARY OF THE INVENTION

A process that can be used to produce an organic anhydride, an organic acid halide, or mixtures thereof is provided. The process comprises contacting a reaction medium with a catalyst in which the reaction medium comprises (1) at least one organic acid, (2) combination of the organic acid and phosgene, (3) combination of at least one organic anhydride and phosgene, or (4) combination of the organic acid, the organic anhydride, and phosgene; and the catalyst is a Group IVB transition metal halide.

DETAILED DESCRIPTION OF THE INVENTION

The contacting of a reaction medium with a catalyst can be carried out under any suitable conditions. Generally, the reaction medium comprising at least one organic acid, mixtures of at least one organic acid and phosgene, or mixtures of at least one organic anhydride and phosgene can be contacted with the catalyst at an elevated temperature under dry conditions and optionally with a solvent. The catalyst is a Group IVb transition metal halide.

The contacting of at least one organic acid with the catalyst produces an acid anhydride or acid anhydrides. The contacting of organic acid with phosgene produces an acid chloride or acid chlorides. An organic acid chloride or acid chlorides can also be produced by contacting at least one organic acid anhydride and phosgene. No aliphatic amide is used in the process of this invention, avoiding the multiple problems of decomposition and corrosivity characterizing the prior art.

The organic acid can be a branched, straight chain, or cyclic alkanoic, alkenoic, or alkynoic acid; or an aryl, alkyl aryl organic acid having one or more carboxylic acids groups; or a mixture of such acids. Examples of suitable organic acids include, but are not limited to, aliphatic carboxylic acids of 2 to about 20 carbon atoms, and aromatic and cycloaliphatic carboxylic acids of 7 to about 24 carbon atoms, per molecule. The suitable acids can contain 1 to 3 carboxyl groups. For example, suitable aliphatic acids include, but are not limited to, acetic acid, butyric acid, lauric acid, palmitic acid, neo-pentanoic acid, propanoic acid, chloroacetic acid, dichloroacetic acid, succinic acid, adipic acid, sebacic acid, acrylic acid, methacrylic acid, succinic acid, and mixtures of two or more thereof; suitable aromatic acids include, but are not limited to, benzoic acid, m-nitrobenzoic acid, isophthalic acid, phthalic, phenylacetic acid, p-chlorobenzoic acid, trans-cinnamic acid, m-toluic acid, terephthalic acid, and mixtures of two or more thereof; suitable cycloaliphatic acid includes, but is not limited to, cyclohexane carboxylic acid; and suitable mixtures of acids are benzoic and terephthalic acids, and isophthalic and terephthalic acids.

The suitable acid anhydrides for the purpose of this invention are anhydrides of the general formulae:

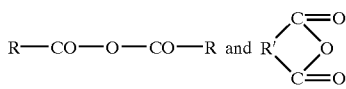

wherein each monovalent R or divalent R' independently represents an organic radical such as a hydrocarbon group. Particularly suitable acid anhydrides are those having an aliphatic, cycloaliphatic, or aromatic group. Thus, R or R' can be alkylene, alkenylene, cycloalkylene, arylene or like divalent, saturated and unsaturated radicals. Preferably, the number of carbon atoms in the R or R' groups is from 1 to 24 and more preferably 1 to 12 per group.

The organic acid anhydride can be any anhydride of the above-listed organic acids. Illustrative acid anhydrides include, among others, acetic anhydride, butyric anhydride, hexanoic anhydride, benzoic anhydride, trimellitic anhydride, octanoic anhydride, chloroacetic anhydride, acrylic anhydride, phenylacetic anhydride, adipic anhydride, sebacic anhydride, nitrobenzoic anhydride, chlorobenzoic anhydride, toluic anhydride, isophthalic anhydride, terephthalic anhydride, succinic anhydride, and mixtures of two or more thereof.

For the purposes of describing this invention, but not to limit the scope of the invention, isophthalic acid and other specific acids and anhydrides are used as example starting materials.

The catalyst is a Group IVb transition metal halide, such as titanium or zirconium tetrachloride or tetrabromide. The term "halide" as used herein to describe the Group IVb transition metal salt refers to chloride or bromide, preferably tetrachloride or tetrabromide. Titanium tetrachloride is the preferred catalyst. These Group IVb metal halides catalyze the conversion of acids to acid anhydrides, and, in the presence of phosgene, the conversion of acid anhydrides to acid chlorides. The novelty and effectiveness of this process stem from the combination of high catalytic activity and the thermal stability of the system. The process of this invention can result in the production of very high purity acid chlorides, the opportunity to recycle catalyst, and environmental and process advantages.

The optional solvent is chosen for inertness in the process. When an acid chloride is the product, the acid chloride is preferably substantially solubile in the solvent. The same solvents can also be used for producing an anhydride. Examples of suitable solvents include, but are not limited to, o-dichlorobenzene, chlorobenzene, heptane, and mixtures of two or more thereof. The acid chloride product can also be used as the solvent, for instance, in the preparation of isophthaloyl chloride from isophthalic acid. Solvents such as chlorobenzene and heptane can be removed from the product stream by fractional distillation. Where the acid chloride is the solvent, no solvent separation is necessary. The acid chloride can be separated by vacuum distillation. In cases where the volatility of the acid chloride is too low for vacuum distillation, other procedures well known to those skilled in the art can be substituted, such as filtration or centrifugation. Additionally the option of driving the conversion to the acid chloride to completion can be available. It should be noted that driving this reaction to completion is typically not practical using the nitrogen-based catalysts of the prior art, such as DMF, due to the tendency for the catalyst-phosgene complex to decompose excessively as reaction conditions are made more severe.

It is important to note that titanium tetrahalide does not react with phosgene as does DMF to form the active species. Rather it catalyzes the conversion of acid to anhydride, wishing not to be bound by theory, most likely by reaction at the isophthalic acid slurry surface to bring into solution a titanium trihalide salt. The mode of action of the Group IVb metal halide catalyst is completely different from that of DMF.

While not wishing to be bound by theory, it is believed that the reaction sequences for the catalyzed reactions of the present invention are described by Reaction Sequence A below, depicting reactions of isophthalic acid. Isophthalic acid, slurried in isophthaloyl chloride, is believed to react at the slurry surface with the $TiCl_4$ catalyst to form the $TiCl_3$ salt (I). The isophthaloyl chloride is effectively the solvent in this case. While isophthalic acid is relatively insoluble in the acid chloride (a property that would limit reaction rates), the $TiCl_3$ salt is readily soluble in the isophthaloyl chloride, passing rapidly into solution where the salt reacts with isophthaloyl chloride to form the anhydrides II and III. In the isophthalic case, the anhydrides are external. Hydrogen chloride, but not carbon dioxide, is liberated in both the salt and anhydride formation steps. In contrast with the acid, the anhydrides are soluble in isophthaloyl chloride. In the presence of phosgene, the anhydrides react stepwise to form first the anhydride/chloride IV and finally two isophthaloyl chloride molecules. In the final two steps, carbon dioxide, but not hydrogen chloride, is liberated.

Reaction Sequence A

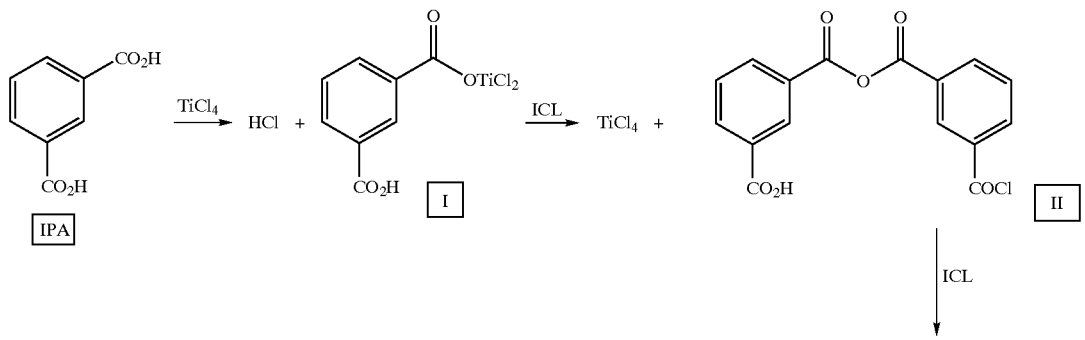

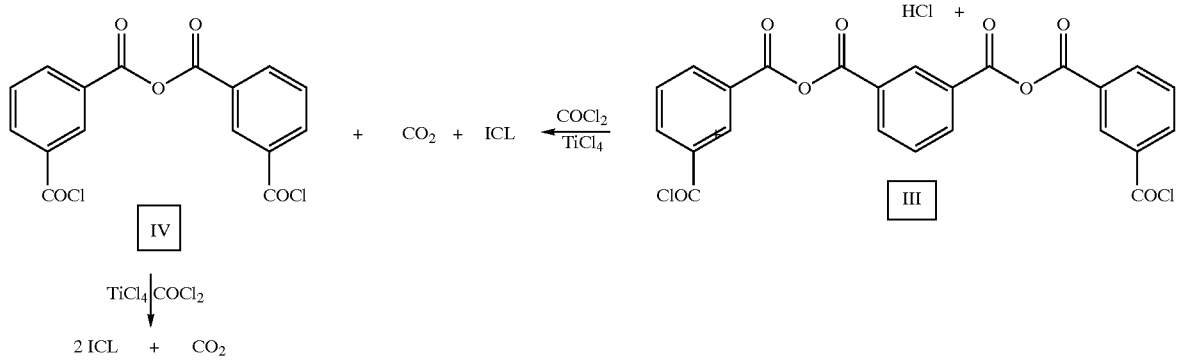

In another embodiment of the invention, terephthalic acid can be contacted with titanium tetrahalide and phosgene to produce terephthaloyl chloride rapidly. Interestingly, if the phosgene is withheld and using titanium tetrachloride, the reaction mass of terephthalic acid and titanium tetrachloride rapidly solidifies as the bicyclic anhydride, in contrast to the isophthalic acid reaction, has a low solubility in the acid and a higher melting point. Reaction of a mixture of terephthalic acid and benzoyl chloride (e.g., a 50/50 molar mixture) with $TiCl_4$ and phosgene avoids the solidification and the mixed acid chlorides are formed. The terephthaloyl chloride can be readily isolated by distillation and the benzoyl chloride recycled. Where a mixture of isophthalic chloride and terephthaloyl chloride is the desired product, isophthalic acid and terephthalic acid (e.g., a 50/50 molar mixture) can be contacted with $TiCl_4$ and phosgene, solidification is prevented, and the reaction proceeds to produce mixed anhydrides, or mixed acid chlorides if phosgene is introduced.

The catalyst can be present in the reaction medium in an effective catalytic quantity. Generally, the amount of $TiCl_4$ or $ZrCl_4$ catalyst used can be about 0.001 to 0.1 moles of catalyst per mole of acid or anhydride, and preferably 0.005–0.05 moles of catalyst per mole of acid or anhydride. The reaction pressure is between 10 mm Hg to 20 atmospheres (130 Pa–200 kPa), and preferably ambient to 10 atmospheres (10 KPa–100 kPa). Increased pressure increases reaction rates by increasing the solubility of phosgene in the reaction mass, and lower or higher pressures can aid in stripping volatile products from the reaction mass or retaining product in the reaction mass. The freezing point of the solvent or reaction mass and the stability limits of the reactants, solvent, and products determine the temperature. Lower temperatures also increase the solubility of phosgene in the reaction mass. Typically, the temperature can be in the range −20° C. to 250° C. and preferably 50° C. to 200° C.

Phosgene can be introduced to the subsurface of the reaction medium with vigorous agitation to maximize gas liquid contact. Vented hydrogen chloride and unreacted phosgene can be conveniently scrubbed using excess 20% aqueous sodium hydroxide solution.

The advantages of the process of this invention include: 1. There are no species involved in the TiCl4 catalysis that provide facile pathways for thermal instability, 2. The evolution of hydrogen chloride in the formation of the anhydrides II and III prior to the introduction of phosgene, and carbon dioxide after the introduction of phosgene, occur separately, 3. The reaction mix of the present invention is substantially less corrosive than the DMF-catalyzed reaction mass, and 4. The Group IVb metal halide catalyst can be readily recovered and reused.

Advantage 1 results in substantially purer acid chloride than is obtained from the DMF-catalyzed process of the prior art. As discussed above, monofunctional impurities can adversely affect the molecular weight of polymers made from acid chloride monomers. Similarly, even traces of color in the acid chloride adversely affect optical grade polymers.

Advantage 2 improves the efficiency with which the evolved hydrogen chloride off-gas may be scrubbed and recycled, since the hydrogen chloride stream is not diluted with a large volume of carbon dioxide.

Advantage 3 allows less expensive materials of plant construction.

Advantage 4 minimizes catalyst cost and eliminates disposal costs for non-recyclable nitrogen-containing catalysts such as DMF.

EXAMPLES

Example 1

$TiCl_4$-catalyzed reaction of isophthalic acid with isophthaloyl chloride in isophthaloyl chloride solvent to form anhydride, followed by $TiCl_4$ catalyzed conversion of the anhydride to isophthaloyl chloride.

The reactor was a 5-neck 1-L round-bottom glass flask, equipped with a heating mantle, an infrared probe for analysis of the reactor contents, a 1000-rpm 4-bladed agitator suitable for efficient gas-liquid contact, a subsurface gas inlet for nitrogen and phosgene, an inlet for catalyst/reactant addition, a temperature probe and an evolved gas outlet. The IR probe was a ReactIR instrument (from Applied Systems, Inc., Millersville Md.). The Fourier transform Infra-red (FTIR) spectrometer captured an infrared spectrum of the reaction mass every two minutes via a wave-guide ending in a Hatelloy C probe with a diamond window subsurface in the reactor. Analysis of the spectra provides data showing the acid, anhydride, acid chloride, and phosgene concentrations during the reaction. The instrument was also provided with a flow through gas cell through which the effluent gas could be routed. This provided quantitative analysis of the hydrogen chloride, carbon dioxide, and phosgene in the effluent. For reactions run in acid chloride as the solvent, the liquid phase spectra could be used for acid and phosgene concentrations, but were not useful for following the formation of acid chloride. The effluent gas analysis of evolved carbon dioxide and hydrogen chloride provided the rate of formation of acid chloride. The evolved gas was discharged to a recirculating packed tower scrubber containing excess 20% aqueous sodium hydroxide solution and serves to remove hydrogen chloride, phosgene, and other volatile acidic chemicals.

To the reactor was added 225 g of isophthaloyl chloride and 15.6 g of isophthalic acid. After heating to 120° C., 0.41 g of titanium tetrachloride was added. The temperature was maintained and conversion of the acid to anhydride was essentially quantitative (98% complete) in 18 minutes. Phosgene was then fed at the rate of 1.0 g/min. Conversion of the anhydride to isophthaloyl chloride was essentially quantitative and was 98% complete in 42 minutes. Essentially all of the titanium tetrachloride was recovered and the isophthaloyl chloride was isolated by distillation through a 6 inch unpacked column, after adding a small amount of o-dichlorobenzene to aid in the separation. The isolated isophthaloyl chloride was 99.89% pure by gas chromatographic analysis. The only impurity at a level >20 ppm was terephthaloyl chloride derived from the terephthalic acid present in the starting material (see Comparative Example A).

Example 2

TiCl4 Catalyzed conversion of isophthalic acid to isophthaloyl chloride in isophthaloyl chloride solvent.

To the reactor described in Example 1 was added 225 g of isophthaloyl chloride and 15.6 g of isophthalic acid. After heating to 120° C., 0.13 g of titanium tetrachloride was added and phosgene fed at the rate of 1.0 g/min. Conversion of the acid to isophthaloyl chloride was essentially quantitative and was 98% complete in 70 minutes.

Example 3

TiCl4 Catalyzed conversion of terephthalic acid to terephthaloyl chloride in terephthaloyl chloride solvent.

To the reactor described in Example 1 was added 225 g of terephthaloyl chloride and 15.6 g of terephthalic acid. After heating to 130° C., 0.52 g of titanium tetrachloride was added and phosgene fed at the rate of 1.0 g/min. Conversion of the acid to terephthaloyl chloride was essentially quantitative and was 98% complete in 46 minutes.

Example 4

$TiCl_4$ Catalyzed reaction of benzoic acid with benzoyl chloride in o-dichlorobenzene solvent to form anhydride, followed by $TiCl_4$ catalyzed conversion of the anhydride to benzoyl chloride.

The procedure of Example 1 was followed using 145 ml of o-dichlorobenzene, 11.5 g of benzoic acid, 13.3 g of benzoyl chloride and 2.05 g of titanium tetrachloride. Both conversions were essentially quantitative. The reaction of the acid with the acid chloride was 98% complete in 20 minutes. The conversion of anhydride to acid chloride was 98% complete in 50 minutes.

Example 5

$TiCl_4$ Catalyzed conversion of benzoic acid to benzoyl chloride in o-dichlorobenzene solvent.

To the reactor described in Example 1 was added 145 ml of o-dichlorobenzene and 23.0 g of benzoic acid. After heating to 120° C., 2.05 g of titanium tetrachloride was added and phosgene fed at the rate of 1.0 g/min. Conversion of the acid to benzoyl chloride was essentially quantitative and was 98% complete in 44 minutes.

Example 6

$ZrCl_4$ Catalyzed conversion of benzoic acid to benzoyl chloride in o-dichlorobenzene solvent.

The procedure of Example 5 was followed, substituting 2.05 g of zirconium tetrachloride for the titanium tetrachloride. Conversion of the acid to benzoyl chloride was essentially quantitative and was 98% complete in 52 minutes.

Example 7

$TiCl_4$ Catalyzed conversion of propionic acid to propionyl chloride in o-dichlorobenzene solvent.

The procedure of Example 5 was followed at 75° C., substituting 14.0 g of propionic acid for the benzoic acid. Conversion of the propionic acid to propionyl chloride was essentially quantitative and was 98% complete in 60 minutes.

Example 8

$TiCl_4$ Catalyzed conversion of acetic acid to acetyl chloride in o-dichlorobenzene solvent.

The procedure of Example 5 was followed at 100° C., substituting 11.3 g of acetic acid for the benzoic acid. Conversion of the acetic acid to acetyl chloride was essentially quantitative and was 98% complete in 50 minutes. The acetyl chloride distilled from the reactor as it formed.

Example 9

$TiCl_4$ Catalyzed reaction of mixed isophthalic and terephthalic acids with acid chloride in mixed isophthaloyl and terephthaloyl chloride solvent to form anhydrides, followed by $TiCl_4$ catalyzed conversion of the anhydride to acid chlorides.

The procedure of Example 1 was followed where the solvent was 112.5 g of isophthaloyl chloride and 112.5 g of terephthaloyl chloride and the acid was 7.8 g of isophthalic acid and 7.8 g of terephthalic acid. The catalyst was 2.1 g of titanium tetrachloride. The acids were converted essentially quantitatively to anhydrides and the anhydrides converted essentially quantitatively to the acid chlorides. Formation of the anhydrides was 98% complete in 44 minutes. Conversion of the anhydrides to acid chlorides was 98% complete in 30 minutes.

Comparative Example A
Product Purity vs. DMF Catalysis

To the reactor described in Example 1 was added 225 g of isophthaloyl chloride and 15.6 g of isophthalic acid. After heating to 100° C., 0.41 g of dimethylformamide was added and phosgene fed at the rate of 1.0 g/min. Conversion of the acid to isophthaloyl chloride was essentially quantitative and was 98% complete in 44 minutes. The distilled isophthaloyl chloride was 99.6% pure by gas chromatic analysis and contained 0.078% m-cyanobenzoyl chloride, 0.10% terephthaloyl chloride and a number of unidentified high boilers at about 0.01% each.

When the isophthalic acid is depleted, the active catalyst, an equimolar complex of dimethylformamide and phosgene, decomposes to tarry products (see for example Parker et al. in U.S. Pat. 3,184,506) and liberates methyl chloride, an air pollutant, and dimethylamine. Dimethylamine is the source of dimethlylcarbamoylbenzoyl chloride, a carcinogen, and m-cyanobenzoyl chloride. M-Cyanobenzoyl chloride cannot be practically separated from isophthaloyl chloride by distillation and is a chain stopper in condensation polymerizations. These undesirable by-products are absent in Examples 1–9 of the present invention.

Comparative Example B
Catalytic Activity vs. Benzoic Acid Thermal Control

The procedure of Example 5 was repeated omitting the catalyst. After 60 minutes, the conversion to acid chloride was only 28% complete, demonstrating the effectiveness of the catalyst of this invention.

Comparative Example C
Catalytic Activity vs. Propionic Acid Thermal Control

The procedure of Example 7 was repeated omitting the catalyst. After 60 minutes, the conversion to acid chloride was only 14% complete, demonstrating the effectiveness of the catalyst of this invention.

Comparative Example D
Catalytic Activity vs. Acetic Acid Thermal Control

The procedure of Example 8 was repeated omitting the catalyst. After 60 minutes, the conversion to acid chloride was only 23% complete, demonstrating the effectiveness of the catalyst of this invention.

What is claimed is:

1. A process for producing acid chloride comprising contacting a reaction medium with a catalyst wherein said reaction medium comprises (1) at least one organic acid and phosgene, (2) at least one organic anhydride and phosgene, or (3) said organic acid, said organic anhydride, and phosgene; and said catalyst is a Group IVB transition metal halide.

2. A process for producing acid anhydride comprising contacting at least one organic acid, optionally in the presence of a solvent, with a catalyst wherein said organic acid is selected from the group consisting of acetic acid, butyric acid, lauric acid, palmitic acid, pentanoic acids, propionic acid, chloroacetic acid, dichloroacetic acid, adipic acid, hexanoic acids, sebacic acid, acrylic acid, methacrylic acid, benzoic acid, m-nitrobenzoic acid, isophthalic acid, phenylacetic acid, p-chlorobenzoic acid, trans-cinnamic acid, m-toluic acid, terephthalic acid, cyclohexane carboxylic acid, succinic acid, and mixtures of two or more thereof; and said catalyst is a Group IVB transition metal halide.

3. A process according to claim 1 wherein said reaction medium comprises said organic acid, phosgene, and optionally a solvent.

4. A process according to claim 1 wherein said reaction medium comprises said organic anhydride, phosgene, and optionally a solvent.

5. A process according to claim 4 wherein said reaction medium further comprises said organic acid.

6. A process according to claim 1, 3, or 5 wherein said organic acid is selected from the group consisting of acetic acid, butyric acid, lauric acid, palmitic acid, pentanoic acids, propionic acid, chloroacetic acid, dichloroacetic acid, adipic acid, hexanoic acids, sebacic acid, acrylic acid, methacrylic acid, benzoic acid, m-nitrobenzoic acid, isophthalic acid, phenylacetic acid, p-chlorobenzoic acid, trans-cinnamic acid, m-toluic acid, terephthalic acid, cyclohexane carboxylic acid, succinic acid, and mixtures of two or more thereof.

7. A process according to claim 2 wherein said organic acid is isophthalic acid, terephthalic acid, combinations of benzoic acid and terephthalic acid, or combinations of isophthalic acid and terephthalic acid.

8. A process according to claim 5 wherein said organic acid is isophthalic acid, terephthalic acid, combinations of benzoic acid and terephthalic acid, or combinations of isophthalic acid and terephthalic acid.

9. A process according to claim 3 or 4 wherein said organic anhydride is selected from the group consisting of acetic anhydride, butyric anhydride, hexanoic anhydride, benzoic anhydride, trimellitic anhydride, octanoic anhydride, chloroacetic anhydride, acrylic anhydride, phenylacetic anhydride, adipic anhydride, sebacic anhydride, nitrobenzoic anhydride, chlorobenzoic anhydride, toluic anhydride, isophthalic anhydride, terephthalic anhydride, pentanoic anhydride, succinic anhydride, and mixtures of two or more thereof.

10. A process according to claim 8 wherein said organic acid is isophthalic acid, terephthalic acid, combinations of benzoic acid and terephthalic acid, or combinations of isophthalic acid and terephthalic acid.

11. A process according to claim 1, 2, 3, 4, or 5 wherein said catalyst is $TiCl_4$, $TiBr_4$, $ZrCl_4$, or $ZrBr_4$.

12. A process according to claim 6 wherein said catalyst is $TiCl_4$, $TiBr_4$, $ZrCl_4$, or $ZrBr_4$.

13. A process according to claim 8 wherein said catalyst is $TiCl_4$, $TiBr_4$, $ZrCl_4$, or $ZrBr_4$.

14. A process according to claim 7 wherein said catalyst is $TiCl_4$ or $ZrCl_4$.

15. A process according to claim 8 wherein said catalyst is $TiCl_4$ or $ZrCl_4$.

16. A process according to claim 9 wherein said catalyst is $TiCl_4$ or $ZrCl_4$.

17. A process according to claim 10 wherein said catalyst is $TiCl_4$ or $ZrCl_4$.

18. A process according to claim 10 wherein said process is carried out at a temperature in the range of from about −25° C. to about 250° C.

19. A process according to claim 12 wherein said process is carried out at a temperature in the range of from about −25° C. to about 250° C.

20. A process according to claim 12 wherein said process is carried out at a temperature in the range of from about −25° C. to about 250° C.

21. A process according to claim 13 wherein said process is carried out at a temperature in the range of from about −25° C. to about 250° C.

22. A process according to claim 15 wherein said process is carried out at a temperature in the range of from about 50° C. to about 200° C.

23. A process according to claim 16 wherein said process is carried out at a temperature in the range of from about 50° C. to about 200° C.

24. A process according to claim 17 wherein said process is carried out at a temperature in the range of from about 50° C. to about 200° C.

25. A process according to claim 21 wherein said process is carried out under a pressure in the range of from about 10 Kpa to about 100 KPa.

26. A process according to claim 22 wherein said process is carried out under a pressure in the range of from about 10 Kpa to about 100 KPa.

27. A process according to claim 23 wherein said process is carried out under a pressure in the range of from about 10 Kpa to about 100 KPa.

28. A process according to claim 24 wherein said process is carried out under a pressure in the range of from about 10 Kpa to about 100 KPa.

* * * * *

UNITED STATES PATENT AND TRADEMARK OFFICE
CERTIFICATE OF CORRECTION

PATENT NO. : 6,429,334 B1
DATED : August 6, 2002
INVENTOR(S) : Gordon L. Thayer, Jr.

It is certified that error appears in the above-identified patent and that said Letters Patent is hereby corrected as shown below:

Column 9,
Line 62, "claim 5" and substitute therefor -- claim 6 --.

Column 10,
Line 1, delete "claim 3 or 4" and substitute therefor -- claim 4 or 5 --.
Line 11, delete "claim 8" and substitute therefor -- claim 9 --.
Line 20, delete "claim 8" and substitute therefor -- claim 9 --.
Line 26, delete "claim 9" and substitute therefor -- claim 10 --.
Line 28, delete "claim 10" and substitute therefor -- claim 11 --.
Line 30, delete "claim 10" and substitute therefor -- claim 11 --.
Line 36, delete "claim 12" and substitute therefor -- claim 13 --.
Line 40, delete "claim 13" and substitute therefor -- claim 14 --.

Signed and Sealed this

Fifth Day of November, 2002

*Attest:*

*Attesting Officer*

JAMES E. ROGAN
*Director of the United States Patent and Trademark Office*